(12) United States Patent
Breuer

(10) Patent No.: US 7,790,436 B2
(45) Date of Patent: *Sep. 7, 2010

(54) METHOD FOR PRODUCTION OF (1S)-3-CHLORO-1-(2-THIENYL)-PROPAN-1-OL USING ALCOHOL DEHYDROGENASE FROM THERMOANAEROBACTER

(75) Inventor: Michael Breuer, Darmstadt (DE)

(73) Assignee: BASF SE, Ludwigshafen (DE)

( * ) Notice: Subject to any disclaimer, the term of this patent is extended or adjusted under 35 U.S.C. 154(b) by 12 days.

This patent is subject to a terminal disclaimer.

(21) Appl. No.: 12/158,526

(22) PCT Filed: Dec. 13, 2006

(86) PCT No.: PCT/EP2006/069629

§ 371 (c)(1),
(2), (4) Date: Jun. 20, 2008

(87) PCT Pub. No.: WO2007/074060

PCT Pub. Date: Jul. 5, 2007

(65) Prior Publication Data

US 2008/0319208 A1 Dec. 25, 2008

(30) Foreign Application Priority Data

Dec. 23, 2005 (DE) .................. 10 2005 062 661

(51) Int. Cl.
*C12P 41/00* (2006.01)
(52) U.S. Cl. ...................................... 435/280
(58) Field of Classification Search ...................... None
See application file for complete search history.

(56) References Cited

U.S. PATENT DOCUMENTS

| 5,362,886 A | 11/1994 | Berglund |
| 7,498,448 B2 * | 3/2009 | Sturmer et al. ............... 549/75 |
| 2007/0083055 A1 | 4/2007 | Sturmer et al. |

FOREIGN PATENT DOCUMENTS

| EP | 0273658 B1 | 7/1988 |
| EP | 0457559 A2 | 11/1991 |
| WO | WO-2005/033094 A2 | 4/2005 |

OTHER PUBLICATIONS

Wong et al., "Enzymes in Synthetic Organic Chemistry", Tetrahedron Organic Chemistry Series vol. 12, Elsevier Science, Inc. Tarrytown, NY, 1994, p. 16.*
Hummel, W., "New Alcohol Dehydrogenases for the Synthesis of Chiral Compounds", Advances in Biochemical Engineering/Biotechnology, 1997, vol. 58, pp. 145-184.
Heiss, C., et al., "Asymmetric Reduction of Ethynyl Ketones and Ethynylketoesters by secondary alcohol dehydrogenase from *Thermoanaerobacter ethanolicus*", J. Chem. Soc., Perkin Trans. 1, 2000, pp. 2821-2825.
Wheeler, W. J., et al., "An Asymmetric Synthesis of Duloxetine Hydrochloride, A Mixed Uptake Inhibitor of Serotonin and Norepinephrine, and its C-14 Labeled Isotopomers", Journal of Labelled Compounds and Radiopharmaceuticals, 1994, vol. XXXVI, No. 3, pp. 213-223.
Stillger, T., et al., "Überwindung von Thermodynamischen Limitierungen in Substratgekoppelten Cofaktor-regenerierungsverfahren", Chemie Ingenieur Technik, 2002, vol. 74, pp. 1035-1039.

* cited by examiner

*Primary Examiner*—Sandra E Saucier
(74) *Attorney, Agent, or Firm*—Connolly Bove Lodge & Hutz LLP

(57) ABSTRACT

A process for preparing optically active (1S)-3-chloro-1-(2-thienyl)propan-1-ol of the formula I

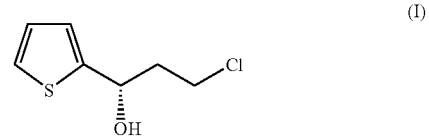

(I)

by, in a medium comprising 3-chloro-1-(2-thienyl)propan-1-one of the formula II

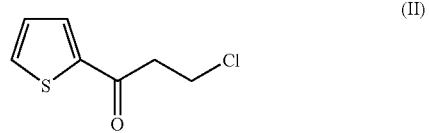

(II)

reducing this compound to the compound of the formula I by means of an alcohol dehydrogenase from the *Thermoanaerobacter* genus, and isolating the product formed in substantially enantiomerically pure form.

4 Claims, No Drawings

METHOD FOR PRODUCTION OF (1S)-3-CHLORO-1-(2-THIENYL)-PROPAN-1-OL USING ALCOHOL DEHYDROGENASE FROM THERMOANAEROBACTER

RELATED APPLICATIONS

This application is a national stage application (under 35 U.S.C. §371) of PCT/EP2006/069629, filed Dec. 13, 2006, which claims benefit of German application 10 2005 062 661.0, filed Dec. 23, 2005.

DESCRIPTION

The present invention relates to a process for preparing optically active (1S)-3-chloro-1-(2-thienyl)propan-1-ol by enzymatic reduction.

PRIOR ART (1S)-3-Chloro-1-(2-thienyl)propan-1-ol is a direct precursor for the preparation of (1S)-3-methylamino-1-(2-thienyl)propan-1-ol ("Duloxetine alcohol"), which is in turn an intermediate in Duloxetine synthesis. Duloxetine® is an active pharmaceutical ingredient which is currently in the process of being approved and is intended for use for indications of depression and incontinence.

EP-B-0273658 describes a process for preparing the corresponding base for Duloxetine by reacting 2-acetylthiophene in a Mannich reaction with formaldehyde and dimethylamine, reduction of the keto group of the resulting Mannich base to the racemic (S)-3-N,N-dimethylamino-1-(thien-2-yl)propan-1-ol, etherification of the alcohol function with naphthyl fluoride and finally conversion of the dimethylamino group to a methylamino function. The desired enantiomer of the naphthyl ether is obtained by use of chiral starting materials or by racemate separation at the stage of the end product, for example via the salts with optically active acids or chromatography on a chiral stationary phase.

U.S. Pat. No. 5,362,886 describes an analogous process in which the racemic propanol obtained at reduction of the keto group is admixed with S-mandelic acid. The resulting S-enantiomer of the alcohol is used in the subsequent reaction stages.

EP-A-0457559 likewise describes a process analogous to EP-B-0273658. Here, the keto group of the Mannich base is reduced with the asymmetric reduction system LAH-lcb (lithium aluminum hydride-[(2R,2S)-(–)-4-dimethylamino-1,2-diphenyl-3-methyl-2-butanol]) to the alcohol in the form of the S-enantiomer. A disadvantage here, in addition to the costs, is the sensitivity of the LAH-lcb reduction system which is stable for only a few minutes.

In Journal of Labelled Compounds and Radiopharmaceuticals, Volume XXXVI, 3, page 213 to 223, W. J. Wheeler and F. Kuo describe a process for preparing Duloxetine. For this purpose, thiophene-2-carbonyl chloride is reacted in a Stille coupling with vinyltri-n-butylstannan in the presence of catalytic amounts of benzylchlorobis(triphenylphosphine)palladium(II) in DMPU (dimethylpropyleneurea) to give 1-(thien-2-yl)propenone of the formula (V)

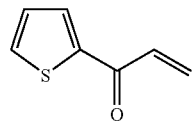

which is subsequently converted by treating with hydrogen chloride to 3-chloro-1-(thien-2-yl)propan-1-one of the formula (VI)

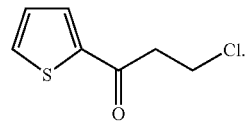

The chloropropanone thus obtained is subsequently reduced using a chiral oxazaborylidine and $BH_3$ to (S)-3-chloro-1-(thien-2-yl)-propan-1-ol of the formula (VII)

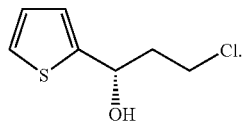

The alcohol thus obtained is converted by successive reaction with sodium iodide and then with methylamine to (S)-3-methylamino-1-(thien-2-yl)propan-1-ol. Subsequent successive reaction with sodium hydride, 1-fluoronaphthalene and hydrogen chloride affords Duloxetine in the form of the hydrochloride.

Hal=halogen

In Chemie Ingenieur Technik (74) pages 1035-1039, 2002, T. Stillger et al. describe substrate-coupled cofactor regeneration processes for enzymatic enantioselective reduction of ethyl 5-oxohexanoate to ethyl (S)-5-hydroxy-hexanoate.

BRIEF DESCRIPTION OF THE INVENTION

It was an object of the invention to find a route for stereospecific reduction of optically active (1S)-3-chloro-1-(2-thienyl)propan-1-ol, in which the reaction process should lead highly quantitatively to the product by an inexpensive route.

This object is achieved by virtue of the surprising finding that it is possible to prepare enzymes with dehydrogenase activity from the Thermoanaerobacter genus, which are capable of stereospecific catalysis of the above reaction.

DETAILED DESCRIPTION OF THE INVENTION

The invention provides a process for preparing optically active (1S)-3-chloro-1-(2-thienyl)propan-1-ol of the formula I

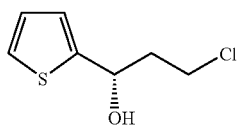

by, in a medium comprising 3-chloro-1-(2-thienyl)propan-1-one of the formula II

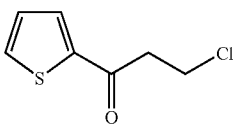

reducing this compound to the compound of the formula I by means of an alcohol dehydrogenase from the *Thermoanaerobacter* genus, and isolating the product formed in substantially enantiomerically pure form.

The enzymes with dehydrogenase activity used in accordance with the invention can be used in the process according to the invention as free or immobilized enzyme.

The process according to the invention is advantageously carried out at a temperature between 0° C. to 95° C., preferably between 10° C. to 85° C., more preferably between 15° C. to 75° C.

The pH in the process according to the invention is advantageously kept between pH 4 and 12, preferably between pH 4.5 and 9, more preferably between pH 5 and 8.

In the process according to the invention, enantiomerically pure or chiral products or optically active alcohols are understood to mean enantiomers which exhibit enantiomeric enrichment. In the process, preference is given to achieving enantiomeric purities of at least 70% ee, preferably of min. 80% ee, more preferably of min. 90% ee, most preferably min. 98% ee.

For the process according to the invention, it is possible to use growing cells which comprise the inventive nucleic acids, nucleic acid constructs or vectors. It is also possible to use quiescent or disrupted cells. Disrupted cells are understood to mean, for example, cells which have been made permeable by means of a treatment with, for example, solvents, or cells which have been disrupted by means of an enzyme treatment, by means of a mechanical treatment (for example French Press or ultrasound) or by means of another method. The crude extracts thus obtained are suitable in an advantageous manner for the process according to the invention. It is also possible to use purified or partly purified enzymes for the process. Immobilized microorganisms or enzymes, which can advantageously find use in the reaction, are likewise suitable.

When free organisms or enzymes are used for the process according to the invention, they are appropriately removed before the extraction, for example by means of a filtration or centrifugation.

The (1S)-3-chloro-1-(2-thienyl)propan-1-ol prepared in the process according to the invention can advantageously be obtained from the aqueous reaction solution by means of extraction or distillation. To increase the yield, the extraction can be repeated more than once. Examples of suitable extractants are solvents such as toluene, methylene chloride, butyl acetate, diisopropyl ether, benzene, MTBE or ethyl acetate, without any restriction thereto.

Alternatively, the (1S)-3-chloro-1-(2-thienyl)propan-1-ol product prepared in the process according to the invention can advantageously be obtained from the organic phase of the reaction solution by means of extraction or distillation or/and crystallization. To increase the yield, the extraction can be repeated more than once. Examples of suitable extractants are solvents such as toluene, methylene chloride, butyl acetate, diisopropyl ether, benzene, MTBE or ethyl acetate, without any restriction thereto.

After concentration of the organic phase, the products can generally be obtained in good chemical purities, i.e. greater than 80% chemical purity. After extraction, the organic phase comprising the product can also be concentrated only partly and the product can be crystallized out. To this end, the solution is advantageously cooled to a temperature of from 0° C. to 10°. The crystallization can also be effected directly out of the organic solution or out of an aqueous solution. The product which has been crystallized out can once again be taken up in the same solvent or in another solvent for another crystallization and crystallized once again. The subsequent advantageous crystallization carried out at least once can further increase the enantiomeric purity of the product if required.

In the workup methods mentioned, the product of the process according to the invention can be isolated in yields of from 60 to 100%, preferably from 80 to 100%, more preferably from 90 to 100%, based on the substrate used for the reaction, for example from 3-chloro-1-(2-thienyl)propan-1-one. The isolated product features a high chemical purity of >90%, preferably >95%, more preferably >98%. Moreover, the products have a high enantiomeric purity which can advantageously, if required, be increased further by the crystallization.

The process according to the invention can be conducted batchwise, semibatchwise or continuously.

The process can advantageously be carried out in bioreactors, as described, for example, in Biotechnology, volume 3, 2nd edition, eds. Rehm et al. (1993), in particular chapter II.

The above description and the examples which follow serve only to illustrate the invention. The numerous possible modifications apparent to the person skilled in the art are likewise comprised by the invention.

The advantage of the process according to the invention lies in the particularly high yield of the optically active alkanol of the formula (I) and of virtually quantitative conversion of alkanone (II).

The enzymatic reduction by means of alcohol dehydrogenase requires cofactors which are consumed in the course of the reaction, i.e. oxidized. A preferred cofactor is NADPH which is oxidized to NADP.

A preferred embodiment of the invention regenerates the cofactors by coupling them with a simultaneous oxidation reaction. For this purpose, particular preference is given to the alkanol/ketone system, in particular isopropanol/acetone, since this is likewise catalyzed by the alcohol dehydrogenase.

The NADPH consumed in the reduction of compound (II) to compound (I) is regenerated again by the enzymatic oxidation of isopropanol to acetone. It should be ensured here that sufficient isopropanol (so-called sacrificial alcohol) is available, and that no excessively high concentrations of acetone which might damage the enzyme are formed.

EXPERIMENTAL PART

Enzyme

The alcohol dehydrogenase from *Thermoanaerobacter* spec. used hereinafter (abbreviated hereinafter to ADH-T) is commercially available and was purchased from Jülich Fine Chemicals (Order No. 90112610, alcohol dehydrogenase T from *Thermoanaerobacter* spec). The ADH-T was used without further purification.

Incubation with NADPH

In one ml of 50 mM $NaH_2PO_4$ buffer (pH 5), 10 mmol of NADPH, 10 μmol of 3-chloro-1-(thien-2-yl)propan-1-one and ADH-T (0.58 mg of protein) were incubated at 30° C. After 60 min, the reaction was ended by adding $HCl_{conc.}$ and the denatured protein was removed by means of centrifugation. After centrifugation, the supernatant was analyzed by chromatography. With reference to the peak areas of reactant and product, the activity of the enzyme can be calculated. Use of chiral chromatography material makes it possible to distinguish the two enantiomers of (1S)-3-chloro-1-(thien-2-yl)propan-1-ol.

Incubation with NADP and Isopropanol (Cofactor Regeneration)

The NADPH cofactor is consumed during the reaction. It is known that the ADH-T performs the oxidation of i-propanol to acetone and can thus regenerate the consumed cofactor. This method is advantageous because NADPH has to be added to the reaction mixture only in catalytic amounts.

In one ml of buffer (50 mM $NaH_2PO_4$ (pH 5) with 10% 2-propanol), 0.2 μmol of NADP, 10 μmol of 3-chloro-1-(thien-2-yl)propan-1-one and ADH-T (0.58 mg of protein) were incubated at 30° C. After 60 min, the reaction was ended by adding $HCl_{conc.}$ and the denatured protein was removed by means of centrifugation. Workup and analysis are effected as described above.

Analysis of (1S)-3-chloro-1-(thien-2-yl)propan-1-ol

The concentration of 3-chloro-1-(thien-2-yl)propan-1-one and 3-chloro-1-(thien-2-yl)propan-1-ol can be determined by means of HPLC. Depending on the selection of the stationary and mobile phase, it is also possible to determine ee value in addition to the concentration.

a) Achiral Analysis

The quantification of the reaction was carried out with the following system:

Stationary phase: Chromolith SpeedROD RP18, 50*4, 6 μm, Merck (Darmstadt) heated to 45° C.

Mobile phase: Eluent A: 10 mM KH2PO4, pH 2.5

Eluent B: acetonitrile

Gradient: 0-0.5 min, 35% B; 0.5-1.0 min 35 to 80% B; 1.0-1.2 min 80% B; 1.2-1.3 min 80%-35% B; 1.3-2.0 min 35% B;

Flow rate: 1.5 ml/min

Detection: UV detection at 230 and 260 nm

Retention times: 3-chloro-1-(thien-2-yl)propan-1-one: approx. 1.6 min 3-chloro-1-(thien-2-yl)propan-1-ol: approx. 1.3 min Authentic material is used to generate a calibration curve, with the aid of which the concentration of unknown samples can be determined.

b) Chiral Analysis

Stationary phase: Chiracel OD-H, 250*4, 6 μm, Daicel, heated to 40° C.

Mobile phase: Eluent A: n-hexane

Eluent B: isopropanol

Isocratic with 2.5% B

Flow rate: 1.0 ml/min

Detection: UV detection at 230 and 260 nm

Retention times: 3-chloro-1-(thien-2-yl)propan-1-one: approx. 9.5 min (1S)-3-chloro-1-(thien-2-yl)propan-1-ol: approx. 16.6 min (1R)-3-chloro-1-(thien-2-yl)propan-1-ol: approx. 18.3 min Authentic material is used to generate a calibration curve, with the aid of which the concentration of unknown samples can be determined.

Result

Reaction without Cofactor Regeneration

After incubation for 60 min, 2.1 mM (1S)-3-chloro-1-(thien-2-yl)propan-1-ol was determined in the reaction mixture. The specific activity of the ADH-T at the start of the reaction is 98 U/g of protein. The resulting alcohol has an ee value of 95%.

Reaction with Cofactor Regeneration

In this system too, the ADH-T is capable of catalyzing both reduction and oxidation reaction by substrate coupling. After incubation for one hour, however, only 0.7 mM (1S)-3-chloro-1-(thien-2-yl)propan-1-ol was found in the reaction mixture. The specific activity of the enzyme at the start of the reaction is also very low at 23 U/g of protein. The resulting alcohol has an ee value of 94%. The relatively low activity can be explained by the possibility that the optimal conditions of the isopropanol oxidation were not present. Possibly, the equilibrium position of the overall reaction is also unfavorable.

Alternatively, the cofactor regeneration can also effect the addition of an auxiliary enzyme, for example a glucose dehydrogenase or formate dehydrogenase. In this case, another second substrate such as glucose or formate is needed instead of isopropanol. Glucose dehydrogenase oxidizes glucose to gluconic acid and, in doing so, reduces the cofactor during the cofactor regeneration with formate dehydrogenase to $CO_2$ as the end product.

What is claimed is:

1. A process for preparing optically active (1S)-3-chloro-1-(2-thienyl)propan-1-ol having formula (I)

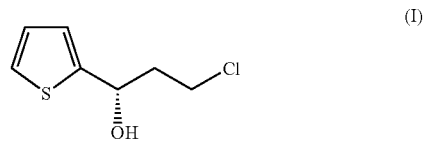

comprising
(1) reducing 3-chloro-1-(2-thienyl)propan-1-one having formula (II)

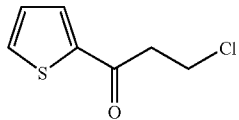

(II)

to said optically active (1 S)-3-chloro-1-(2-thienyl)propan-1-ol having formula (I) with an alcohol dehydrogenase from the Thermoanaerobacter genus in the presence of a cofactor; and (2) isolating said 3-chloro-1-(2-thienyl)propan-1-one having formula (II) formed in substantially enantiomerically pure form;

wherein said reduction is conducted in a medium comprising said 3-chloro-1-(2-thienyl) propan-1-one having formula (II).

2. The process of claim 1, wherein said cofactor is NADPH.

3. The process of claim 2, wherein said cofactor is regenerated in the reduction.

4. The process of claim 3, wherein said regeneration is carried out by the enzymatic oxidation of isopropanol.

* * * * *